United States Patent
Haj-Ahmad

(10) Patent No.: US 8,063,199 B2
(45) Date of Patent: Nov. 22, 2011

(54) METHOD FOR ISOLATING BOTH FREE AND PROTEIN ASSOCIATION DNA

(75) Inventor: Yousef Haj-Ahmad, Thorold (CA)

(73) Assignee: Norgen Biotek Corp., Thorold, ON (CA)

( * ) Notice: Subject to any disclaimer, the term of this patent is extended or adjusted under 35 U.S.C. 154(b) by 186 days.

(21) Appl. No.: 12/160,941

(22) PCT Filed: Jan. 15, 2007

(86) PCT No.: PCT/CA2007/000057
§ 371 (c)(1),
(2), (4) Date: Mar. 23, 2009

(87) PCT Pub. No.: WO2007/079594
PCT Pub. Date: Jul. 19, 2007

(65) Prior Publication Data
US 2010/0063266 A1    Mar. 11, 2010

(30) Foreign Application Priority Data
Jan. 16, 2006  (CA) ..................................... 2533052

(51) Int. Cl.
*C07H 21/00*  (2006.01)
(52) U.S. Cl. ................. 536/25.41; 536/25.3; 536/25.31; 536/25.4
(58) Field of Classification Search ........................ None
See application file for complete search history.

(56) References Cited

U.S. PATENT DOCUMENTS
5,534,054 A * 7/1996 Woodard et al. ......... 106/287.11
6,177,278 B1 * 1/2001 Haj-Ahmad .................... 436/94

OTHER PUBLICATIONS

Irina Botezatu et al., Genetic Analysis of DNA Excreted in Urine: A New Approach for Detecting Specific Genomic DNA Sequences from Cells Dying in an Organism, Clinical Chemistry 46:8 1078-1084 (2000).
Gypsyamber D'Souza et al., Analysis of the Effect of DNA Purification on Detection of Human Papillomavirus in Oral Rinse Samples by PCR, Journal of Clinical Microbiology, vol. 43, No. 11, Nov. 2005, p. 5526-5535.
Gary A. Fahle et al., Comparison of Six Commercial DNA Extraction Kits for Recovery of Cytomegalovirus DNA from Spiked Human Specimens, Journal of Clinical Microbiology, vol. 38, No. 10, Oct. 2000, p. 3860-3863.
A.M. Hossain et al., Modified guanidinium thiocyanate method for human sperm Dna isolation, Molecular Human Reproduction, Vol. 3, No. 11, pp. 953-956, 1997.
Ying-Hsiu Su, Human Urine Contains Small, 150 to 250 Nucleotide-Sized, Soluble DNA Derived from the Circulation and May Be Useful in the Detection of Colorectal Cancer, Journal of Molecular Diagnostics, vol. 6, No. 2, May 2004.

* cited by examiner

*Primary Examiner* — Patrick Lewis
(74) *Attorney, Agent, or Firm* — Harris, Shelton, Hanover & Walsh

(57) ABSTRACT

A method is disclosed for isolating both free and protein-associated DNA from bodily fluids, such as urine, saliva, serum, tears, sweat, cerebral spinal fluid, and plasma. The method comprises as a first step concentrating and isolating both the free DNA and the proteins present in the bodily fluid. The proteins are then digested in order to release the formerly protein-associated DNA from the isolated proteins. Lastly, the free and formerly protein-associated DNA can be isolated and purified.

16 Claims, 3 Drawing Sheets

METHOD FOR ISOLATING BOTH FREE AND PROTEIN ASSOCIATION DNA

This is a U.S. National Phase Application under 35 USC 371 and Applicant herewith claims the benefit of PCT/CA2007/000057 accorded an international filing date of Jan. 15, 2007 which was published in English as WO2007/07594 on Jul. 19, 2007 and Canadian patent application no. 2,533,052 filed Jan. 16, 2006 (hereby specifically incorporated by reference).

FIELD OF THE INVENTION

The invention relates to methods for isolating both free and protein-associated total DNA from bodily fluids.

BACKGROUND OF THE INVENTION

The use of DNA for diagnostics has seen a steady increase in recent years. The means of obtaining, isolating and analyzing the DNA have been extensively studied. A number of methods for the isolation of the DNA are extremely intrusive, such as the use of amniocenteses for the isolation of fetal blood, or biopsies to isolate genetic material associated with tumors for cancer diagnosis and monitoring. These methods are often painful and can lead to possible complications. Thus there exists a need to develop a less intrusive and safer way to isolate DNA for diagnostic uses.

It has recently been discovered that human urine contains sub microgram per milliliter amounts of DNA (Su et al., 2004). This DNA has been found to be comprised of two main types of DNA from two different sources. The larger species is generally greater than 1 kbp in size, and appears to be derived mainly from cells shed into the urine from the urinary tract. The second species is smaller, generally between 150 and 250 bp, and is mostly recovered from the supernatant. Researchers have found that this smaller species of urine DNA derives, at least in part, from the circulation.

It has been determined that some of this circulating DNA is a result of cell death. Upon cell death, cellular components are dismantled and usually phagocytosed by macrophages or neighboring cells. The nuclear DNA is often degraded by a range of enzymes, producing nucleosomes and their oligomers. In human adults, approximately $10^{11}$ cells die daily as a result of either disease or apoptosis. This corresponds to approximately 0.6 grams of DNA being released from the cells. It has been found that some of this DNA from dying cells escapes intracellular degradation and phagocytosis, and is able to circulate in the bloodstream. Then, some of this DNA from the bloodsteam is able to cross the kidney barrier and ends up in urine (Botezatu et al., 2000).

It is not currently known how small DNA can cross the kidney barrier. The nature of the cell-free DNA in blood has been extensively studied. Nucleosome-sized circulating DNA might originate from the internucleosomal cleavage of chromatin, a major hallmark of apoptosis. Malignant, benign, or even pre-neoplastic cells often proliferate at abnormal rates that are accompanied by an increase in cell death, and this DNA may also accumulate in the urine.

The circulating DNA from the bloodstream that passes into the urine can be isolated and used in many different applications in diagnostics. The DNA can be used for molecular diagnostics and prognosis, including cancer testing, prenatal diagnosis, and transplantation monitoring (U.S. Pat. Nos. 6,492,144 and 6,251,638). There are a number of advantages to using the DNA found in bodily fluids, such as urine, saliva, serum, tears, sweat, cerebral spinal fluid and plasma, for diagnostics, for example many of these fluids can be collected by non-invasive methods.

Classical methods of isolating DNA from urine generally require a large amount of urine, and result in the isolation of only a small amount of DNA. One of the most traditional methods of isolating urine DNA involves centrifuging 10 mL of urine, resuspending the pellet in a small volume of the urine supernatant, adding lysis solution that contains proteinase K, and incubating for up to 4 hours at 55° C. After incubation, the sample is extracted once with TE phenol, twice with phenol:chloroform:isoamyl alcohol and once with chloroform:isoamyl alcohol. Finally, sodium acetate is added to the sample, it is precipitated with ethanol overnight, washed with 70% ethanol the next day and resuspended in TE buffer. This method is long, tedious and often results in only trace amounts of DNA being isolated (Yokota et al., 1998).

In another published method for isolating DNA from urine (Su et al., 2004), urine samples are added to 1.5 volumes of 6M guanidine thiocyanate and mixed by inversion. A resin is then added to the sample and incubated for 2 hours. The resin-DNA complex is then centrifuged, transferred to a minicolumn, washed with a buffer and the DNA eluted with water. Again, this method requires large amounts of urine and results in only small amounts of DNA being isolated.

Much of the DNA present in urine is protein-bound, while only a small portion of the urine DNA is free in the urine. With the classical approaches, including those outlined above, only the free DNA is being isolated. Since free DNA constitutes only a small portion of the total DNA present in urine, the yields using these classical approaches will be low and consequently large volumes of urine will be required to isolate sufficient urine DNA to be used in downstream applications. In other words, only a sub-population of the total DNA from urine is isolated. Given that a significant amount of the DNA present in urine is protein-bound, in order to isolate total DNA from urine one must isolate both the free DNA and the proteins present in the urine, and then release the bound DNA from these proteins. The existing methods rely on protein elimination and DNA retention in the first and subsequent steps, inevitably resulting in a loss of a significant amount of protein bound DNA.

Thus, there exists a need for a novel method to isolate pure and biologically active total DNA from small amounts of bodily fluids, including urine, serum, saliva, tears, sweat, cerebral spinal fluid and plasma.

BRIEF SUMMARY OF THE INVENTION

It is now an object of the present invention to provide a novel method to isolate pure and biologically active total DNA, including both free and protein-associated DNA, from small amounts of bodily fluids. The method will involve the use of conditions in which both the urinary proteins with associated DNA and the free DNA are first isolated, with the subsequent release of the bound DNA from the proteins. This is contratry to all current methods for the isolation of DNA from urine, in which the proteins and protein-bound DNA are discarded and only the free DNA is isolated. This new method will result in larger quantities of total DNA being isolated from small volumes of urine or other bodily fluids.

Accordingly, the invention provides a method for isolating both free and protein-associated DNA from the bodily fluid by first concentrating and isolating the free DNA and proteins present in the urine, then digesting the proteins in order to release the protein-associated DNA from the isolated proteins, and lastly isolating and purifying the total DNA. The method used to concentrate and isolate the free DNA and proteins may include dialysis, precipitation, binding the free DNA and proteins to a resin that is either packed into a column or in slurry form, or any other traditional method that is known in the art to concentrate and isolate proteins. The proteins can then either be digested in solution, or digested while they are bound to a resin in either a column or slurry format. The released DNA can then be isolated by precipitation, binding it to a resin that is either packed in a column or in a slurry format, or through any other traditional methods of DNA isolation that are known in the art.

BRIEF DESCRIPTION OF SEVERAL VIEWS OF THE DRAWINGS

In drawings which illustrate by way of example only a preferred embodiment of the invention.

DETAILED DESCRIPTION OF THE INVENTION

Figure 1:
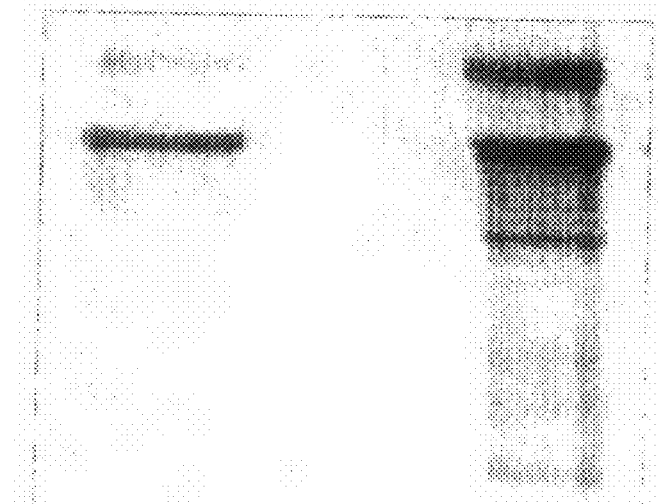
FIG. 1 is an SDS-PAGE gel showing the input, flowthrough and elution of urine proteins when using a silicon carbide column to concentrate and purify the proteins.

The primary objective of the exemplary methods carried out was the isolation of both free and protein-associated DNA from bodily fluids by first isolating the free DNA and urine proteins, subsequently digesting the proteins, and then isolating the released DNA.

One preferred embodiment of the method involves the use of columns containing silicon carbide (SiC) in order to isolate the free DNA and proteins present in the bodily fluids. The first step in the preferred embodiment is the collection of a sample of bodily fluid. Generally, between 1 and 3 mL of urine will be collected into a tube that contains protease inhibitors and sodium azide. Once collected, a volume of NaOH, citric acid and phosphoric acid is added to the urine in order to adjust the pH to 3.5. Once the urine sample has been prepared, the SiC column is activated using 500 µL of the same solution. Once activated, the prepared urine sample is then loaded onto the column in order to bind both the free DNA and urine proteins. The column is then washed with NaOH, citric acid and phosphoric acid, and the free DNA and proteins are eluted into a small volume of tribasic sodium phosphate.

Once the proteins have been eluted, they can be digested using known chemicals and enzymes, including pronase, proteinase K and SDS. In one preferred embodiment, the proteins are digested using pronase, proteinase K and SDS. Following digestion, the sample is mixed with guanidine hydrochloride and loaded onto another column containing particles of silicon carbide. In this case, both the free and released DNA will bind to the SiC while the remaining protein fragments and other contaminants will be removed in the flowthrough. The column is then washed using ethanol and TE buffer, and the purified DNA is eluted in a small volume of 10 mM Tris-HCl. The purified DNA can then be used in a number of downstream applications, including PCR for the purpose of diagnostics.

In another preferred embodiment, the urine sample is collected and prepared in the same way as stated above. The sample is again applied to a column containing particles of silicon carbide, and the free DNA and urine proteins are bound to the column and washed using NaOH, citric acid and phosphoric acid. At this point, the proteins are digested while still bound to the column using proteinase K. After the protein digestion has been completed, the column is washed using guanidine hydrochloride, in order to remove the digested proteins and other contaminants. Lastly, the purified total DNA is then eluted from the SiC using Tris-HCl. This DNA can be used in a number of downstream applications, including PCR for the purpose of diagnostics for identifying and monitoring disease states.

The above preferred embodiments can also be applied in the same way to silicon carbide particles that are in a slurry. The slurry may be made with water, guanidine hyrdrochloride or any other applicable substance. The above embodiments can also be applied to particles other than silicon carbide that are able to bind either proteins, DNA or both. Different compositions of solutions can also be used for any of the methods stated above. A person skilled in the art should recognize that many different particles and solutions can be used for the purposes of this procedure, to isolate both free and protein-associated DNA from urine.

EXAMPLES

These examples are described for the purposes of illustration and are not intended to limit the scope of the invention.

Example 1

In an exemplary embodiment of one step of the invention, free DNA and urine proteins are isolated using a column that is packed with silicon carbide particles. Prior to use, the column must be activated. This is achieved by adding 500 µL of a solution comprised of 22.5 mM NaOH, 12.5 mM citric acid and 12.5 mM phosphoric acid to the column, and centrifuging at 3,300×g for 2 minutes. This step is repeated a second time in order to activate the column. The urine sample is then prepared by collecting it into a tube containing a mixture of protease inhibitors and 100 mM sodium azide. Once the sample is collected, it's pH is adjusted to 3.5 using the solution containing NaOH, citric acid and phosphoric acid. Generally, a small volume of the solution is added to the urine, it is mixed and the pH is tested. This is repeated until the desired pH of 3.5 is reached. Once prepared, the sample is loaded onto the activated column by spinning at 3,300×g for 2 minutes. The column is then washed twice with 500 µL of the same NaOH, citric acid and phosphoric acid solution, again spinning at 3,300×g for 2 minutes. After washing, the free DNA and the urine proteins, including proteins which have DNA associated, are eluted from the column by spinning 50 µL of Tris-HCl (pH 8.5) through the column for 2 minutes at 3,300×g. The elution is repeated a second time, resulting in 100 µL total elution.

It has been found that this method for isolating and concentrating urine proteins results in a high degree of concentration, without the loss of any urine proteins in the flowthrough. This has been determined by running SDS-PAGE gels of the input urine proteins, the flowthrough, and the elution.

FIG. 1 is an SDS-PAGE gel showing the input, binding flowthrough and elution of urine proteins when concentrated and purified using a silicon carbide column. Lane A of the gel represents the proteins present in the input urine, Lane B represents the flowthrough from the binding step, and Lane C represents the eluted urine proteins.

Example 2

In an exemplary embodiment of one step of the invention, free DNA and urine proteins would have previously been isolated by one of the described methods, such that the proteins would be in solution. Typically, the urine proteins are then digested using 5 mg/mL pronase, 0.1 mg/mL proteinase K and 5% SDS. The mixture is incubated at 60° C. overnight, in order to allow for full digestion of the proteins.

Example 3

In an exemplary embodiment of one step of the invention, free DNA and urine proteins are isolated using a column that is packed with silicon carbide particles. Prior to use, the column must be activated. This is achieved by adding 500 µL of a solution comprised of 22.5 mM NaOH, 12.5 mM citric acid and 12.5 mM phosphoric acid to the column, and centrifuging at 3,300×g for 2 minutes. This step is repeated a second time in order to activate the column. The urine sample is then prepared by collecting it into a tube containing a mixture of protease inhibitors and 100 mM sodium azide. Once the sample is collected, it's pH is adjusted to 3.5 using the solution containing NaOH, citric acid and phosphoric acid. Generally, a small volume of the solution is added to the urine, it is mixed and the pH is tested. This is repeated until the desired pH of 3.5 is reached. Once prepared, the sample is loaded onto the activated column by spinning at 3,300×g for 2 minutes. The column is then washed twice with 500 µL of the same NaOH, citric acid and phosphoric acid solution, again spinning at 3,300×g for 2 minutes.

At this point, 75 µL, of digesting buffer is then loaded onto the column to allow for digestion of the bound urine proteins. This digesting buffer contains 5 mg/mL pronase, 0.1 mg/mL proteinase K and 5% SDS. The buffer is added to the column, and the column spun at 2,000×g for 5 minutes. If any solution has passed through the column into the collection tube, it is transferred back into the column using a pipette. The column is then incubated at 60° C. for 2 hours in order to allow for the digestion of the proteins.

Example 4

In an exemplary embodiment of the invention, free DNA and urine proteins would have been previously isolated by one of the described methods, and digested in solution. The sample is then prepared for loading onto a SiC column in order to purify the total urine DNA (both free and formerly protein-associated) by mixing it with 5 volumes of 1M guanidine hydrochloride. Once prepared, the sample is bound to the SiC column by spinning at 14,000×g for 1 minute. The column is then washed twice with 500 µL of wash buffer, containing 70% ethanol and TE buffer. The wash solution is added to the column, and the column spun at 14,000×g for 1 minute for each wash. After the washing step is completed, the column is spun at 14,000×g for 1 minute, in order to dry the column and remove any residual traces of ethanol. Next, 25 µL of 10 mM Tris-HCl (pH 8.5) is added to the column, and the column spun at 14,000×g for 1 minute to elute the purified DNA. The elution is repeated again into the same tube, giving a total of 50 µL of purified DNA to be used in diagnostic downsteam applications.

Figure 2:
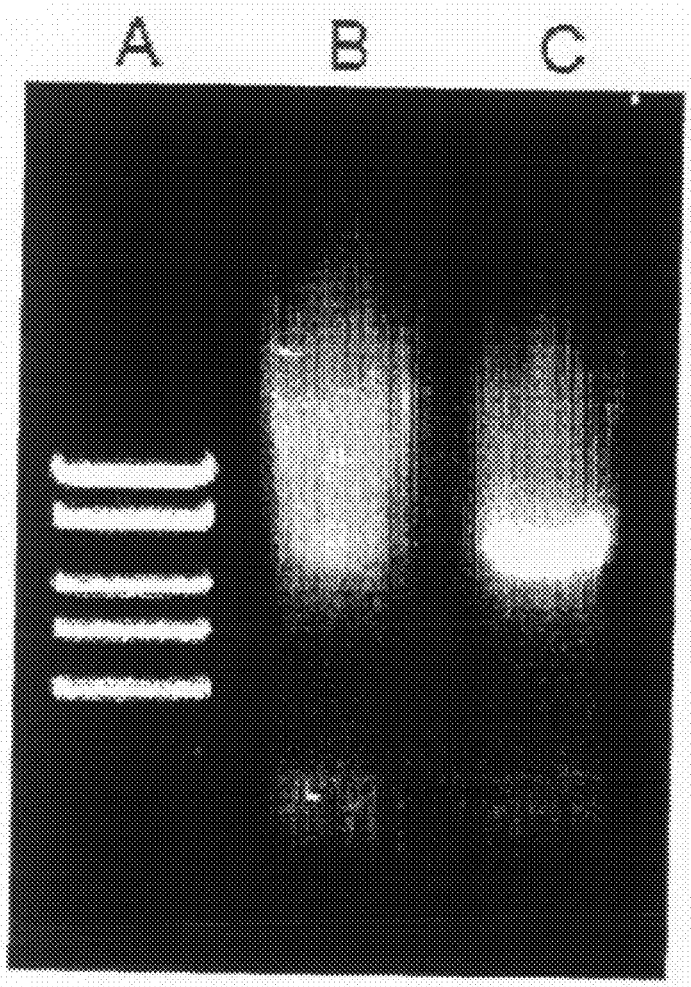
FIG. 2 is an agarose gel showing both the free and protein-associated DNA isolated from 2 mL of human urine.

FIG. 2 is an agarose gel showing the total DNA isolated from 2 mL of human urine. In this particular example, the free DNA and urine proteins were first isolated and concentrated by binding them to a column containing particles of silicon carbide. Following elution, the proteins were digested using a combination of pronase, proteinase K and SDS. The resulting (free and formerly protein-associated) DNA was then isolated and purified by binding to a second column containing silicon carbide. Lane A is a molecular weight marker, while lanes B and C contain DNA isolated from two different 2 mL samples of human urine.

Example 5

In an exemplary embodiment of the invention, the free and protein-associated DNA from 4 different urine samples would have been isolated and purified in accordance with the invention. This (free and formerly protein-associated) DNA can then be shown to be intact and biologically active by using it as a template in a PCR reaction. The PCR is based on U.S. Pat. No. 6,251,638, (hereby specifically incorporated by reference) in which a nested PCR is performed in order to detect Y-chromosome sequences in the urine of pregnant females. This test can be used to determine the sex of a fetus. The urine samples used were from a male, from a non-pregnant female, and from 2 pregnant females. Primers were generated based on Y-chromosome specific sequences. The PCR mixture was then made, and contained the following:

10 µL urine DNA sample
1 µL Pfu polymerase
6 µL forward primer (5 µM)
6 µL reverse primer (5 µM)
10 µL buffer with $MgSO_4$
3 µL dNTPs
64 µL water The PCR was then performed using the following program:
5 min@95° C.
45 sec@60° C.
45 sec@72° C.
45 sec@94° C.
45 sec@60° C.
4 min@72° C.

Upon completion of the PCR, 5 µL of the product was run on an agarose gel to determine if the Y specific sequences were present. The first round of PCR results in a 154 by product. Some of the PCR product was also used as the template in a second, nested PCR reaction. The second reaction used the same composition and program as the first PCR, but used new primers which were internal to the first set of primers used. Again, this PCR was used to detect Y-specific sequences in the maternal urine, and results in both the 154 by product being generated, as well as the 77 by nested PCR product.

In this case, the DNA isolated from male urine was used as a positive control, and resulted in the generation of PCR products. The DNA isolated from the non-pregnant female served as the negative control, and did not result in the generation of a PCR product. In the case of the DNA isolated from the 2 pregnant women, the DNA from the first sample resulted in the generation of PCR products, while the DNA from the second sample did not result in the generation of a PCR product. Thus, it can be concluded that the first woman is carrying a male fetus, while the second woman is carrying a female fetus. Thus the DNA isolated using this preferred embodiment of the invention is biologically active, and can be used in diagnostics to determine fetus sex by PCR.

Figure 3:
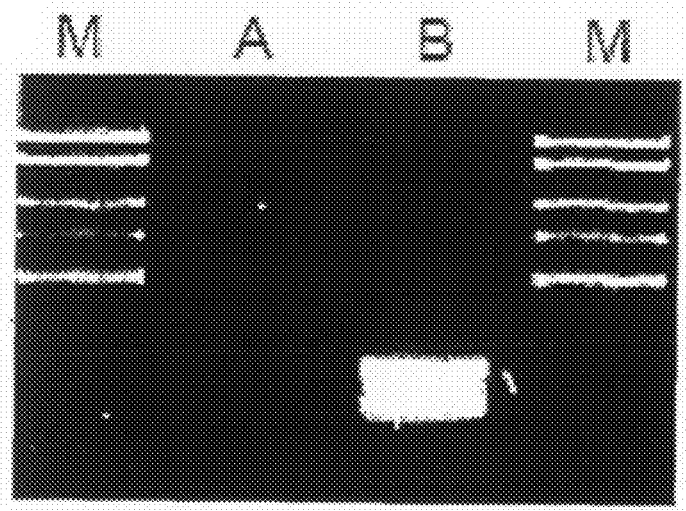
FIG. 3 is an agarose gel showing PCR amplification of total DNA isolated from urine, indicating that the DNA is biologically active.

FIG. 3 is an agarose gel showing PCR amplification of protein-associated DNA isolated from urine. PCR was performed as per Botezatu et al. (2000; U.S. Pat. No. 6,251,638), in which Y-chromosome specific sequences were targeted using a nested PCR procedure. DNA was isolated from 2 mL of male human urine, by first concentrating and isolating the urine proteins and free DNA using a column packed with silicon carbide particles. The urine proteins were then digested to release the DNA, and the released and free DNA were subsequently purified using a second silicon carbide column. Generally, 10 µL of purified DNA was then used as the template in the PCR reaction. Lanes A and C are molecular weight markers, Lane B is the initial 154 bp PCR product, and Lane C contains the nested PCR product from the second round of amplification, which comprises both the 154 bp product as well as the 77 bp nested PCR product. Thus the isolated DNA is of a high quality, and can be used in downstream applications including PCR.

Using the inventive techniques and methods described above, it would be obvious to one skilled in the art that such methods can be used to isolate total DNA, including both free and protein-associated DNA, from other bodily fluids. Such bodily fluids include saliva, serum, tears, sweat, cerebral spinal fluid, and plasma.

Various embodiments of the present invention have been thus described in detail by way of example, however it will be apparent to those skilled in the art that variations and modifications may be made without departing from the invention. The invention includes all such variations and modifications as fall within the scope of the appended claims.

What is claimed is:

1. A method for isolating both free and protein-associated DNA from a bodily fluid comprising: a) first concentrating and isolating both free DNA and proteins present in the bodily fluid; b) digesting the proteins in order to release protein-associated DNA from the isolated proteins; and c) isolating the free and released total DNA.

2. The method of claim 1 wherein the bodily fluid is selected from saliva, serum, tears, sweat, cerebral spinal fluid and plasma.

3. The method of claim 1 wherein the bodily fluid is urine.

4. The method of claim 1 wherein the free DNA and protein associated DNA are concentrated using a method selected from dialysis, precipitation, binding to a resin packed into a column, and binding to a resin in a slurry format.

5. The method of claim 4 wherein the resin is silicon carbide.

6. The method of claim 1 wherein the proteins can be digested while still bound to the resin.

7. The method of claim 1 wherein the proteins can be digested while in solution.

8. The method of any one of claim 1 wherein the free and formerly protein-associated DNA is isolated by one method of precipitation, binding to a resin packed into a column, or binding to a resin in a slurry format.

9. The method of claim 8 wherein the resin is silicon carbide.

10. The method of claim 3 wherein the bodily fluid is between 1 and 3 ml.

11. A method for isolating both free and protein-associated DNA from a urine comprising: a) contacting the solution containing the both free and protein-associated DNA with silicon carbide at a binding pH for the both free and protein-associated DNA to allow the both free and protein-associated DNA to bind to the silicon carbide; b) exposing the silicon carbide of step (a) to an elution pH for the both free and protein-associated DNA to allow the both free and protein-associated DNA to be eluted from the silicon carbide into an eluate;

and c) recovering the free and protein-associated DNA from the eluate; d) digesting the proteins in order to release protein-associated DNA from the isolated proteins; and e) isolating the free and released total DNA.

12. The method of claim 11 wherein the binding pH is 3.5.

13. The method of claim 11 wherein the elution pH is 8.5.

14. A method for isolating both free and protein-associated DNA from a bodily fluid comprising: a) contacting the solution containing the both free and protein-associated DNA with silicon carbide at a binding pH for the both free and protein-associated DNA to allow the both free and protein-associated DNA to bind to the silicon carbide; b) digesting the proteins in order to release protein-associated DNA from the isolated proteins c) eluting the free and released total DNA; and d) isolating the free and released total DNA.

15. The method of claim 14 wherein digesting the proteins in order to release protein-associated DNA from the isolated proteins occurs by adding proteinase K to said column.

16. The method of claim 14 further comprising the step of adding guanidine hydrochloride to remove the digested proteins.

* * * * *